US00PP08186P

United States Patent [19]

Nobbio

[11] Patent Number: Plant 8,186

[45] Date of Patent: Mar. 23, 1993

[54] CARNATION NAMED NOBGIAC

[75] Inventor: Giacomo Nobbio, San Remo, Italy

[73] Assignee: Selecta Klemm KG, Hanfacker, Fed. Rep. of Germany

[21] Appl. No.: 733,212

[22] Filed: Jul. 19, 1991

[51] Int. Cl.[5] ..... A01H 5/00

[52] U.S. Cl. ..... Plt./73.1

[58] Field of Search ..... Plt./70.1, 71.1, 73.1

*Primary Examiner*—Howard J. Locker

*Attorney, Agent, or Firm*—Tilton, Fallon, Lungmus & Chestnut

[57] ABSTRACT

A new standard carnation particularly distinguished by its continuous and profuse production of medium sized blooms of a solid Signal Red color borne singly on strong upright stems having a length of 90 to 100 cm. with moderately abundant foliage and growing from a vigorous upright bush having a total height of about 150 cm. and having a very rapid growth habit.

1 Drawing Sheet

BACKGROUND OF THE NEW PLANT

This new carnation variety originated as a a hybrid seedling produced by me at my nursery at San Remo, Italy, by my crossing of an unnamed variety selected from my collection of carnation plants maintained at my nursery for breeding purposes with pollen from the carnation variety "Lontarion", U.S. Plant Pat. No. 5,435 being grown at my nursery. The object of this crossing was the production of a fast growing and vigorous bush with a normal branching habit producing flower stems of substantial length; the plant being grown in greenhouse to provide a continuous and profuse production of flowers the year around. This particular seedling was selected for propagation because of its bright Signal Red colored flowers produced on a plant having a vigorous upright growth habit and initial propagation was done by means of cuttings with such success that such propagation was continued for several successive generations which proved its retention of the novel characteristics of the parent plant and that its homogeneity was well established for commercial production of the new variety which is now being carried on in Germany, Italy and Israel.

DESCRIPTION OF THE DRAWING

My new standard carnation is illustrated by the accompanying full color photographic drawing which shows flower stems of the new plant with buds in several stages of development, a face view of a mature flower in full bloom, flower petals and a calyx from which the flower petals have been removed, the colors shown being as close to that herein specified as is possible to obtain by conventional photographic procedures.

DESCRIPTION OF THE NEW PLANT

The following is a detailed description of my new carnation plant based upon observation of plants grown in greenhouse at San Remo, Italy with color designations according to The R.H.S. Color Chart of The Royal Horticultural Society of London, England.

THE PLANT

Origin: Seedling.

Parentage:

*Seed parent.*—House Variety No. M 15 Red (unpatented).

*Pollen parent.*—The carnation variety "Lontarion" (U.S. Plant Pat. No. 5,435).

Classification:

*Botanic.*—*Dianthus caryophyllus.*

*Commercial.*—Standard carnation.

Form: Vigorous, upright bush.

Height: At least 150 cm.

Growth rate: Rapid.

Cane length: 90 to 100 cm.

Branching character: Normal.

Growth: Vigorous and upright with very good strength.

Foliage:

*Quantity.*—Moderate.

*Number of leaves.*—About 20 pairs.

*Size of leaf.*—Moderate. At fifth node, 15 cm. long and 0.8 cm. wide.

*Shape.*—Oblong with entire margins.

*Texture.*—Smooth.

*Color.*—Upper side — Blue Green. Under side — Blue Green.

THE BUD

Size: Medium.

Diameter: About 20 to 25 mm.

Length: About 35 mm.

Form: Cylindrical.

Rate of opening: Moderate.

Color:

*When sepals first divide.*—Orange Red.

*When petals begin to unfurl.*—Orange Red.

Sepals:

*Number.*—5.

*Shape.*—Ovoid with acute apex.

*Character.*—The sepals curl back when flowers open.

*Color.*—Inside — Light Green. Outside — Grey Green.

Calyx:

*Shape.*—Campanulate.

*Size.*—Moderate, about 28 mm. wide and 35 mm. long.

*Aspect.*—Smooth.

*Splitting.*—The calyx does not split.

Flower stem:

*Length.*—About 90 to 100 cm.
*Character.*—Erect and rigid.
*Color.*—Blue Green.

THE FLOWER

Blooming habit: Continuous and profusely the year around, grown as a standard greenhouse variety.
Size of bloom: Medium.
*Diameter.*—About 8 to 8.5 cm.
*Depth.*—About 5 to 5.5 cm.
Borne: Singly on a strong upright stem.
Shape:
*When bloom first opens.*—Flat.
*When bloom matures.*—High center.
Petalage:
*Number of petals.*—80 to 100.
*Arrangement.*—Imbricated.
*Form.*—Reniform with dentate margins.
*Texture.*—Soft.
*Appearance.*—Satiny.
*Color.*—Entire body of all petals and both sides — Signal Red 43-A.
Persistence: The petals hang on and dry and bloom stays upright.
Fragrance: None.
Disease resistance: Resistant to *Fusarium oxysporum* as observed in Netherlands and Germany.
Lasting quality:
*On plant.*—15 days; as cut flower — about 12 days.

THE REPRODUCTIVE ORGANS

Stamens:
*Number.*—2 to 4.
*Arrangement.*—Erect around the ovary.
*Anthers.*—None.
*Filaments.*—Length: About 18 cm. Color: Whitish.
*Pollen.*—None.
Pistils:
*Number.*—3.
*Styles.*—Length: About 20 to 30 mm. Color: Light Pink.
*Stigmas.*—Color: Light pink.
Character of the ovaries: Rhomboid in shape with ribbed surface; color of the upper part, Green; color of the lower part, Cream.

THE FRUIT

Fertility: The fruit is fertile.
Shape: Ovoid.
Color at maturity: Brown.

I claim:

1. The new and distinctive standard carnation substantially as herein shown and described, particularly characterized by its continuous and profuse production of medium sized Signal Red colored flowers borne on strong upright stems of a tall bush having normal branching, a fast growth rate and moderately abundant foliage.

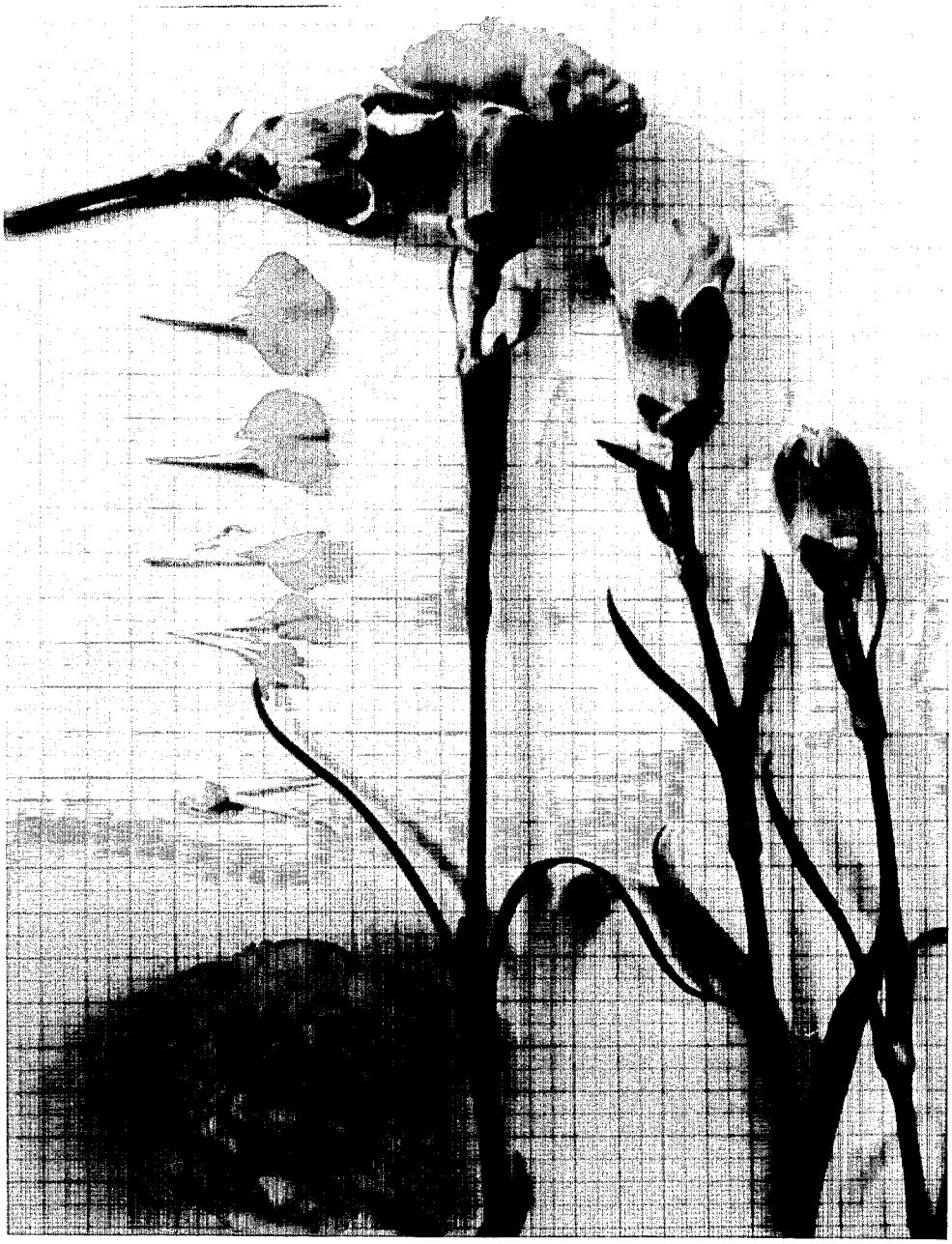

* * * * *